(12) United States Patent
Feussner et al.

(10) Patent No.: US 6,875,847 B1
(45) Date of Patent: Apr. 5, 2005

(54) LINOLEATE AND LINOLENATE-LIPOXYGENASE MUTANTS

(75) Inventors: Ivo Feussner, Halle (DE); Ellen Hornung, Halle (DE)

(73) Assignee: Institut fur Pflanzenbiochemie IPE, Halle (DE)

( * ) Notice: Subject to any disclaimer, the term of this patent is extended or adjusted under 35 U.S.C. 154(b) by 0 days.

(21) Appl. No.: 09/937,908

(22) PCT Filed: Mar. 22, 2000

(86) PCT No.: PCT/EP00/02545

§ 371 (c)(1),
(2), (4) Date: Jan. 7, 2002

(87) PCT Pub. No.: WO00/60093

PCT Pub. Date: Oct. 12, 2000

(30) Foreign Application Priority Data

Mar. 30, 1999 (DE) ......................... 199 14 464

(51) Int. Cl.$^7$ ................................................ C07K 1/00
(52) U.S. Cl. ..................................................... 530/370
(58) Field of Search ......................................... 530/370

(56) References Cited

PUBLICATIONS

Feussner et al., "All three acyl moieties of trilinolein are efficiently oxygenated by recombinant His–tagged lipid body lipoxygenase in vitro," *FEBS Letters, 431* (3), 433–436 (Jul. 24, 1998).

Hornung et al., "Conversion of cucumber linoleate 13–lipoxygenase to a 9–lipoxygenating species by site–directed mutagenesis," *PNAS USA, 96* (7), 4192–4197 (Mar. 30, 1999).

Patent Abstracts of Japan, 012 (338) (C–527) (Sep. 12, 1988) & JP 63–098392 A (Agency of Ind. Science & Technology) (Apr. 28, 1988).

Patent Abstracts of Japan, 014 (497) (C–0774) (Oct. 30, 1990) & JP 02–207792 (Agency of Ind. Science & Technology) (Aug. 17, 1990).

Prigge et al., "Structure conservation in lipoxygenases: structural analysis of soybean lipoxygenase–1 and modeling of human lipoxygenases," *Proteins, 24* (3), 275–291, (Mar., 1996).

Sloane et al., "Conversion of human 15–lipoxygenase to an efficient 12–lipoxygenase: the side–chain geometry of amino acids 417 and 418 determine positional specificity," *Protein Engineering, 8* (3), 275–282 (Mar., 1995).

Steczko et al., "Conserved histidine residues in soybean lipoxygenase: functional consequences of their replacement," *Biochemistry, 31* (16), 4053–4057 (Apr. 28, 1992).

*Primary Examiner*—Elizabeth McElwain
(74) *Attorney, Agent, or Firm*—Leydig, Voit & Mayer, Ltd.

(57) ABSTRACT

The present invention concerns a procedure for the manufacture of plant lipoxygenases with altered positional specificity as well as the lipoxygenase obtained through the procedure and its use for the hydroperoxylation of substrates. In particular the LOXs according to the invention permit for the first time the manufacture of new γ-linolenic acid derivatives in large quantity. For this γ-linolenic acid as substrate is incubated under suitable conditions with the LOXs according to the invention. Depending on the mutant LOXs put into use a hydroperoxylation of the γlinolenic acid then ensues, preferably at position 6 or position 9 or positions 6 and 9.

4 Claims, 7 Drawing Sheets

9-LOX

13-LOX

Retention time (minutes)

FIG. 5

```
  1  MFGIGKNIIE GALNTTGDLA GSVINAGGNI LDRVSSLGGN KIKGKVILMR SNVLDFTEFH
 61  SNLLDNFTEL LGGGVSFQLI SATHTSNDSR GKVGNKAYLE RWLTSIPPLF AGESVFQINF
121  QWDENFGFPG AFFIKNGHTS EFFLKSLTLD DVPGYGRVHF DCNSWVYPSG RYKKDRIFFA
181  NHVYLPSQTP NPLRKYREEE LWNLRGDGTG ERKEWDRIYD YDVYNDIADP DVGDHRPILG
241  GTTEYPYPRR GRTGRPRSRR DHNYESRLSP IMSLDIYVPK DENFGHLKMS DFLGYTLKAL
301  SISIKPGLQS IFDVTPNEFD NFKEVDNLFE RGFPIPFNAF KTLTEDLTPP LFKALVRNDG
361  EKFLKFPTPE VVKDNKIGWS TDEEFAREML AGPNPLLIRR LEAFPPTSKL DPNVYGNQNS
421  TITESHIKHG LDGLTVDEAM KQNRLYIVDF HDALMPYLTR MNATSTKTYA TRTLLLLKDD
481  GTLKPLVIEL ALPHPQGDQL GAISKLYFPA ENGVQKSIWQ LAKAYVTVND VGYHQLISHW
541  LHTHAVLEPF VIATHRQLSV LHPIHKLLVP HYKDTMFINA SARQVLINAN GLIETTHYPS
601  KYSMELSSIL YKDWTFPDQA LPNNLMKRGL AVEDSSAPHG LRLLINDYPF AVDGLDIWSA
661  IKTWVQDYCC LYYKDDNAVQ NDFELQSWWN ELREKGHADK KHEPWWPKMQ TLSELIESCT
721  TIIWIASALH AAVNFGQYPY GGYILNRPTT SRRFMPEVGT AEYKELESNP EKAFLRTICS
781  ELQALVSISI IEILSKHASD EVYLGQRASI DWTSDKIALE AFEKFGKNLF EVENRIMERN
841  KEVNLKNRSG PVNLPYTLLV PSSNEGLTGR GIPNSISI
```

(SEQ ID NO: 1)

Retention time (minutes)

LINOLEATE AND LINOLENATE-LIPOXYGENASE MUTANTS

The present invention concerns a process for the manufacture of plant lipoxygenases with altered positional specificity, together with the lipoxygenase produced by the procedure and its use in the hydroperoxylation of substrates.

The LOXs (linolenic acid: oxygen oxidoreductase; EC.1.13.11.12; LOXs) are widely distributed in the plant and animal domains (Siedow, J. N. (1991) Ann. Rev. Plant Physiol. Plant Mol. Biol. 42, 145–188; Yamamoto S. (1992) Biochem. Biophys. Acta 1128, 117–131). These enzymes represent a family of iron-containing dioxygenases which catalyse a regional (or positional) and stereoselective oxygenation of polyunsaturated fatty acids to hydroperoxy-derivatives (Rosahl, S. (1996) Z. Naturforsch. 51c, 123–138). In mammals LOXs are classified according to their specificity for particular positions in the oxygenation of arachidonic acid (Yamamoto, S. (1992) Biochem. Biophys. Acta 1128, 117–131; Schewe, T., Rapaport, S. M. & Kühn, H. (1986) Adv. Enzymol. Mol. Biol. 58, 191–272). Since arachidonic acid is not present in higher plants, or only in limited quantities as a component of stored lipids, LOXs from plants are classified as 9- and 13-LOXs. This nomenclature derives from the position in the linoleic acid (LA) at which the oxygenation takes place (Gardner, H. W. (1991) Biochem. Biophys. Acta 1084, 221–239). Lately a comprehensive classification of plant LOXs on the basis of a comparison of primary structures has been proposed (Shibata, D. & Axelrod, B. (1995) J. Lipid Mediators Cell Signal. 12, 213–228). The specificity of a LOX for a particular position is the result of two catalytic partial reactions:

(i) of the regional and stereospecific removal of hydrogen, by which, in fatty acids containing several double bonds (such as linolenic acid, arachidonic acid or icosapentic acid) hydrogen removal in various positions can result.

Figure 1:
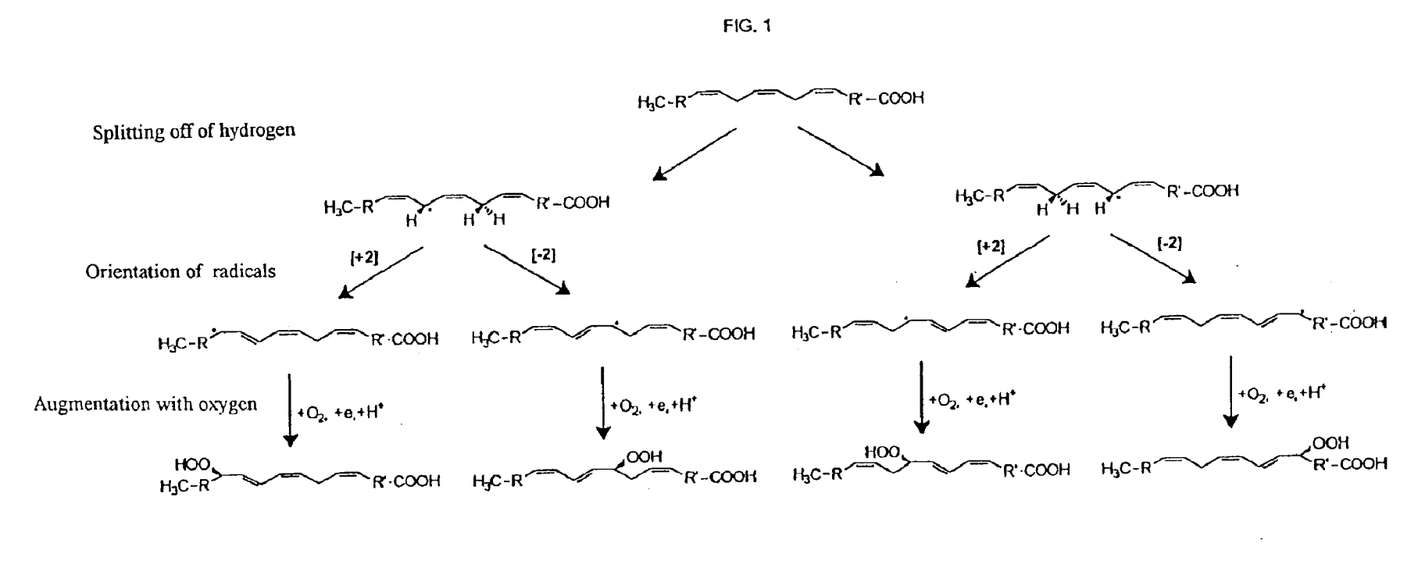
FIG. 1 shows the specificity of a LOX reaction with substrates containing two allylic methylenes.

(ii) of the regional and stereospecific insertion of oxygen (by which the oxygen can be inserted in various positions (the +2 and −2 position) (compare FIG. 1). In that way a fatty acid with 3 double-allylic methylenes, such as arachidonic acid can be oxygenated from a LOX to 6 regioisomeric hydroperoxy derivatives (HPETEs), that is, to 15- and 11-HPETE (these arise from the removal of hydrogen at position C-13), 12- and 8-HPETE (these arise from the removal of hydrogen at position C-10) and 9- and 5-HPETE (these arise from the removal of hydrogen at position C-7). Experiments with 12- and 15-LOX from mammals show that the position of the hydrogen removal can be altered if critical amino-acids are changed through directed mutagenesis (Borngraber S., Kuban R. J, Anton, M. & Kuhn H. (1996) J. Mol. Biol. 264, 1145–1153; Sloane, D. L. Leung, R., Craik, C. S. & Sigal, E. (1991) Nature 354, 149–152). Attempts to change the LOX reactivity from a +2 to a −2 rearranging from or vice verse (e.g. converting a linoleate 13-LOX to a 9-LOX) with the assistance of directed mutagenesis have so far not been successful.

The technical problem underlying the present invention was to provide a method by which the required positional specificity of the LOX could be made available.

This problem is solved according to the invention through a process by which one or more amino-acids undergo substitution in a wild-type LOX.

In a preferred embodiment the exchange of the amino-acids takes place in the region of the amino-acid position 527 to 536 or 593 to 602 of the LOX from *Cucumis sativus* or a corresponding position in a LOX from a different plant species. The amino-acid positions given above refer to the sequence under the access in number X92890 in the NIH data bank "Entrez" or the sequence according to FIG. 5. The positions in other LOXs corresponding to the amino-acid positions 527 to 536 or 593 to 602 of the lipoxygenase from *Cucumis sativus* in LOXs from other plant species can easily be determined by sequence comparisons between the sequence X92890 and the further protein sequences such as from soya beans, potatoes, *Arabidopsis*, tobacco or barley. The following Table 1 shows the result of an amino-acid comparison between the enzyme originating from cucumber and the corresponding positions in the enzymes from other plants. The first group (13-LOX) shows a comparison between LOXs which insert a hydroperoxy group at position 13, while the second group (9-LOX) shows a comparison between groups which insert a hydroperoxy residue at position 9.

TABLE 1

Comparison of amino-acid residues which are presumably involved in the specificity of a plant LOX for a particular position (13 and/or 9).

| ENZYME | Access no. | Position of amino-acid residue | Amino-acid residue |
| --- | --- | --- | --- |
| 13-LOX | | | |
| Cucumber lipid body LOX | X92890 | 596/597 | Thr/His |
| LOX-1 from soya beans | P08170 | 556/557 | Thr/Phe |
| LOX-H1 from potatoes | X96405 | 614/615 | Ser/Phe |
| LOX-2 from *Arabidopsis* | P38418 | 611/612 | Cvs/Phe |
| 9-LOX | | | |
| LOX from potatoes | P37831 | 579/580 | Thr/Val |
| Elicitor-induced LOX from tobacco | X84040 | 580/581 | Thr/Val |
| LOX-A from barley grain | L3 5 931 | 574/575 | Thr/Val |

The sequence at position 527 to 536 reads TVNDVGY-HQL (SEQ ID NO: 2) according to the single-letter code for amino-acids in the deposited sequence X92890. The sequence at position 593 to 602 reads IETTHYPSKY (SEQ ID NO: 3) (sequence according to X92890).

In an especially preferred embodiment the substitution at position 531 and/or 597 results in the sequence X92890. At position 531 in the wild type a Val-residue and at position 597 a His-residue are found.

In a further preferred embodiment the residue at position 531 is replaced by a Phe- or a His-residue and at position 597 by a Val- or a Phe-residue.

Most particularly preferred is an embodiment in which the substitution at position 531 represents a Val->Phe and at position 597 a His->Val substitution. Preferably in each case only one of the substitutions mentioned takes place in a given wild type. In that way the substitution in the region of amino-acid positions 527 to 536 leads to the conversion of the 13-LOX from the lipid bodies of Cucumis sativus to a γ-linolenic acid 6-LOX, while the substitution at position 597 leads to conversion of the linolenic acid 13-LOX to a linolenic acid 9-LOX. Subsequently both these mutants are described as V531F and H597V. The wild-type sequence is shown as FIG. 5. Positions 531 and 597 are indicated.

Preferably the exchange of amino-acids is performed in the wild-type with the aid of directed mutagenesis, as is known in the state of the art (cf. e.g. Feussner, I., Bachmann, A., Höhne, M.& Kindl, H. (1998) FEBS Lett. 431, 433436).

The present invention concerns in addition LOX mutants which are obtainable by the above-mentioned process.V531F and H597V are the preferred mutants, as explained in more detail above. The LOXs according to the invention are manufactured with the aid of known state-of-the-art procedures such as directed mutagenesis and the associated protein expression.

Furthermore the present invention concerns nucleic acids coding for the LOXs according to the invention. Proceeding from the state-of-the-art available wild-type sequences, the sequences according to the invention can be constructed though directed mutagenesis.

The present invention furthermore concerns vectors into which the nucleic acids according to the invention are introduced with the aim of cloning and expression. Corresponding cloning and expression vectors are adequately known to the skilled person from the present state of the art (cf. Maniatis et al. Molecular Cloning: a Laboratory Manual (1989), Cold Spring Harbor Laboratory Press).

The present invention concerns in addition a cell into which the nucleic acid according to the invention or the vector according to the invention is inserted. Following insertion of the nucleic acid or the vector the cell is then in a position to express a LOX for the first time or in an increased quantity. In this way the fatty acid pattern of a cell can be specifically altered, with the result that the phenotype of the cell can be altered in various respects. Among other things this may include a different composition of the cell membrane.

Finally, from the abovenamed cells new plants or plant parts can be generated through in vitro cultivation procedures. For the construction of such transgenic plants the well-known transformation system based on the Agrobacteria and Ti-plasmid derivatives can for example be used.

The LOXs according to the invention permit for the first time the manufacture of new γ-linolenic acid derivatives in large quantity. For this, γ-linolenic acid as substrate is incubated under suitable conditions with the LOXs according to the invention. Depending on the inserted LOX mutant, hydroperoxylation of the γ-linolenic acid then preferably occurs at position 6 or position 9 or positions 6 and 9.

Especially preferred is a γ-linolenic acid derivative containing a hydroperoxy group at position 6. The derivative can then be converted easily into the hydroxy derivative.

Such a γ-linolenic acid derivative has not been accessible hitherto, since it lacked a LOX with suitable position specificity.

Further examples serve as illustration of the invention.

1. Manufacturing the Mutant H597V

Materials:

The chemicals used were drawn from the following sources: the standards for chiral and racemic hydroxy fatty acids came from Chayman Chem (Ann Arbor, Mi, USA) and trilinolein (TL) from Sigma, Deisenhofen (Germany). Methanol, hexane, 2-propanol (all of HPLC grade) came from Baker (Griesheim, Germany). Restriction enzymes were obtained from New England Biolabs (Schwalbach, Germany).

Directed Mutagenesis and Protein Expression:

For the bacterial expression of wild-type LOX and for directed mutagenesis the plasmid pQE-30 (Qiagen, Hilden, Germany), which contained the cDNA of the LOX from lipid bodies of cucumber cotyledons as an insert (LOXpQE 30: cf. Feussner, I., Bachmann, A., Höhne, M. & Kindl, H. (1998) FEBS Lett. 431, 433–436) was used. The mutagenesis was carried out with the aid of the QuikChange Mutagenesis Kit from Stratagene (Heidelberg, Germany). Oligonucleotides with the appropriate base exchanges were obtained from MWG-Biotech (Ebersberg, Germany). For the analysis of the mutations further conservative base exchange was initiated in order to create new restriction division sites or to delete existing ones. In addition all the mutations were sequenced and at least three different bacterial clones expressed and used for the investigation of enzymatic properties. The expression of LOXpQE-30 and all the mutations was carried out according to Feussner, I., Bachmann, A., Höhne, M. & Kindl, H. (1998) FEBS Left. 431, 433–436. Cells from 1-liter cultures were resuspended in 5 to 7 ml lysis buffer and with the aid of an ultrasound needle broken up with pulses each of 30 seconds, and the cell debris made into pellets. The affinity purification of the polyHis-extended LOX was carried out as previously described (cf. Feussner, I., Bachmann, A., Höhne, M. & Kindl, H. (1998) FEBS Lett. 431, 433436).

Activity Assay and Preparation of Samples:

For product analysis 0.9 ml of the cell lysate was incubated at room temperature for 30 minutes with 0.9 mM LA, 0.9 mM γ-linolenic acid or 1.2 mM trilinolein (end concentration) in 100 mM tris buffer pH 7.5. The reactions were stopped by the addition of sodium borhydride, to convert the hydroperoxy fatty acids to the corresponding hydroxy compounds. The tests were acidified to pH 3 and the lipids were extracted (cf. Bligh, E. G. & Dyer, W. J. (1959) Can. J. Biochem. Physiol. 37, 911–917). The lower chloroform phase was recovered and the solvent medium steamed off. The remaining lipid was dissolved in 0.1 ml methanol and aliquots subjected to HPLC analysis. For the alkaline hydrolysis of triacyl glycerine the lipid extracts were diluted with 0.4 ml methanol. Eighty μl of 40% (w/v) KOH was added and the samples were incubated for 20 minutes at 60° C. under an argon atmosphere. After cooling off to room temperature the tests were acidified with glacial acetic acid and the aliquots analysed by RP-HPLC.

Analysis:

The HPLC analysis was carded out with a Hewlett Packard 1100 HPLC system coupled to a diode detector. The RP-HPLC of free fatty acid derivatives was carried out on a Nucleosil C-18 column (Macherey-Nagel, 250×4 mm, 5 μm particle size) with a solvent system of methanol/water/acetic acid (85/15/0.1; v/v/v) and a flow rate of 1 ml/min. The absorptions at 234 nm (absorption of the conjugated double bond system of the hydroxy fatty acids) and at 210 nm (polyunsaturated fatty acids) were correspondingly recorded. Triacyl glycerine, which contains oxygenated LA, was separated on a Nucleosil C-18 column (Macherey-Nagel, Düren, Germany; 250×4 mm, 5 μm particle size) using a binary gradient system. The system included as, solution A:

methanol/water/acetic acid (90/10/0.1, v/v/v), and as solution B methanol/acetic acid (100/0.1, v/v/v), and the following gradient programme was run through: 10 minutes at 100% solution A, then over 20 minutes with a linear increase of solution B to 100% solution B, followed by an isocratic run of 50 minutes at 100% solution B. The absorption at 234 nm was recorded. The direct phase HPLC (SP-HPLC) of hydroxy fatty acid isomers was carried out on a Zorbax SIL column (HP, Waldbronn, Germany; 250×4 mm, 5 µm particle size) with a solvent system of n-hexane/2 propanol/acetic acid (100/2/0.1 v/v/v) at a flow rate of 1 ml/minute. The enantiomer composition of the hydroxy fatty acids was analysed with the aid of chiral-phases-HPLC on a Chiralcell-OD column (Daicel Chem. Industrie, sales department of Baker Chem., Deventer, The Netherlands; 250×4.6 mm, 5 µm particle size) with a solvent system of hexane/2-propanol/acetic acid (100/5/0.1, v/v/v) at a flow rate of 1 ml/min. (cf Feussner, I., Balkenhohl, T. J., Porzel, A., Kühn, H. & Wasternack, C. (1997) J. Biol. Chem. 272, 21635–21641).

Modelling the Enzyme/Substrate Exchange Activity Through Alteration of the Structure with the aid of Directed Mutagenesis:

The structure investigations carried out on numerous lipoxygenases from a variety of sources and own investigations established that position 597, the one His residue from the lipid bodies carried by the cucumber, could be an appropriate point of attack for altering the positional specificity of 13-LOX. Consequently the mutant H597V was constructed with the aid of directed mutagenesis. The wild-type and the mutant were over-expressed as polyHis-prolonged fusion protein purified on a nickel-sepharose column. As expected, the HPLC analysis of the oxygenated LA product with the wild-type enzyme produced 13-H(P)ODE as main product (cf. FIG. 4). For the mutant H597V, however, 9-H(P)ODE was identified as the main product. A further mutant was constructed, in which the His residue at position 597 has been replaced by a further amino-acid, in which the further amino-acid residue occupies a greater volume than valine but a smaller volume than histidine. The mutant H597M was constructed. This mutant also showed a strong preference for the formation of 9-H(P)ODE. The kinetic characterization of the wild-type in accordance with 13-LOX and the 9-LOX mutant H597M showed that the mutation led to a greatly increased substrate affinity and a reduction in the reaction speed. For the wild-type enzyme a $K_M$ of 114.9 µM and an LA turnover at $V_{max}$ condition (substrate saturation) of 12 s$^{-1}$ were determined (23 points were measured between 100 µM and 250 µM LA concentration). In contradistinction to that a $V_{max}$ of 2 s$^{-1}$ and a $K_M$ of 1333.3 µM were calculated for the H597M mutant (21 points were measured between 300 µM and 1400 µM LA concentration). These data indicate that the substrate binding could be vigorously hindered by the mutant, so that more substrate is necessary to reach $V_{max}$. A further mutation was investigated in which a mutant was produced with the polar threonine at position 596 being replaced by an isoleucine, which is smaller but does not contain a polar hydroxy group. This mutant was catalytically active (comparable with the wild-type enzyme) but happened to show a scattered position specificity.

Specificity of the Reaction with Trilinolein:

Earlier investigations of the substrate specificity with LOX from the lipid bodies of the cucumber indicated the capacity of the enzyme to oxygenate esterified polyunsaturated fatty acids (cf. Feussner, I., Bachmann, A., Höhne, M. & Kindl, H. (1998) FEBS Left. 431, 433–436; Feussner, I., Balkenhohl, T. J., Porzei, A., Kühn, H. & Wasternack, C. (1997) J. Biol. Chem. 272, 21636–21642). Since triacyl glycerine contains no free carboxyl groups, no actual differences are expected if the pattern of the oxygenation products of the wild-type are compared with the 9-LOX mutants. In fact it is found that the wild-type enzyme and the 9-LOX mutants show trilinoleate-13-LOX activity. Nevertheless the rates of trilinolein oxygenation by the 9-LOX mutants were only 50% of the activity measured for the wild-type enzyme. Furthermore the trilinolein oxygenation by the mutated enzyme led in fact to triacyl glycerine variants in which an LA residue was oxygenated. By contrast, with the wild-type enzyme all 3 linoleic acid residues were oxygenated (cf. FIG. 7).

2. Manufacturing LOX Mutants:

The reagents and procedures used in the manufacture of these mutants were in fact those described above for the H597V mutant. In what follows some deviations from the abovenamed procedure, which were specially adapted for the manufacture of the V531 F mutant, are explained.

Directed Mutagenesis and Protein Expression

Figure 6:
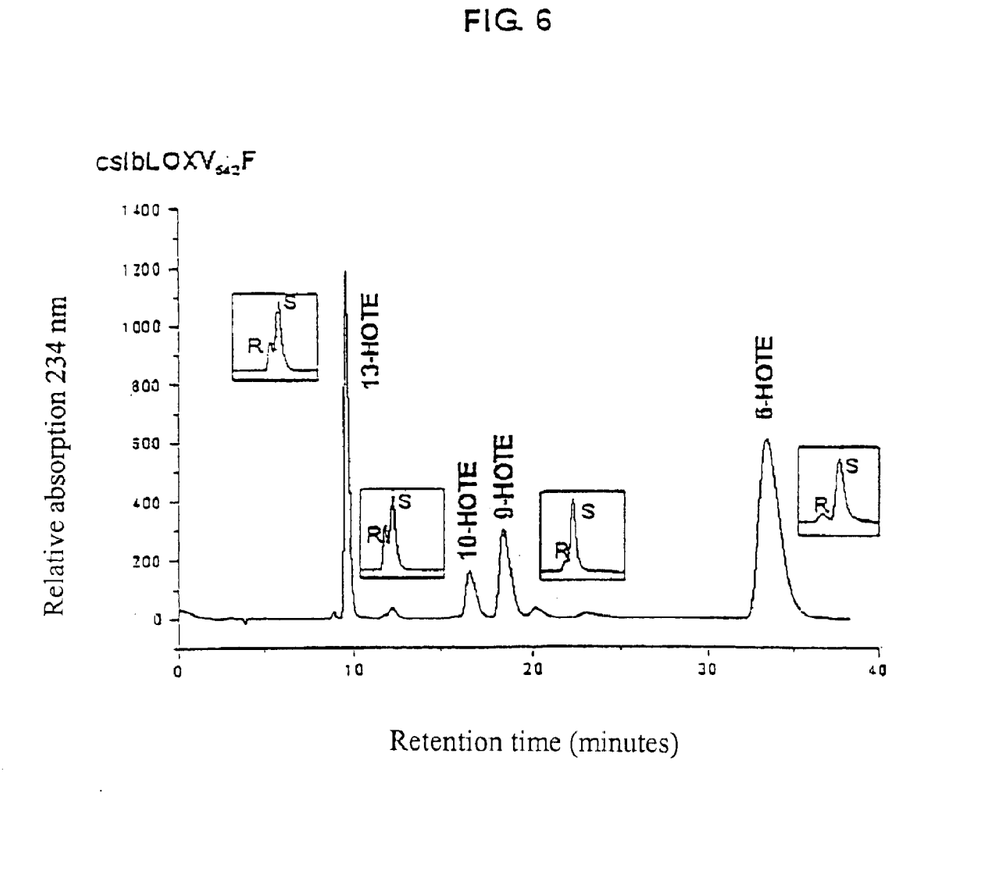
FIG. 6 shows the HPLC analysis of hydroxylated fatty acids obtained with the aid of the mutant V531F from γ-linolenic acid.

The initial cDNA and the mutagenesis kit were as described above. For the analysis of the mutation further conservative base exchanges were carried out in order to produce a new restriction site for BstEll. For the manufacture of the V531F mutation the following primer was used: GCT TAT GTA ACT GTT AAT GAT TTC GOT TAC CAT CAA CTT ATT AGT CAT TGG TTG CAT AC (SEQ ID NO: 4) (coding strand) and GTA TGC AAC CAA TGA CTA ATA AGT TGA TGG TAA CCG AAA TCA TTA ACA GTT ACA TAA (SEQ ID NO: 5) (complementary strand). In addition the mutant was sequenced and 3 different bacterial colonies were expressed and used for the enzymatic investigations. The expression of LOXpQE-30 was carried out as described previously. The further processing also continued as already described above. The analysis of the fatty acid derivatives produced (the one hydroperoxy group contained in position 6) also continued as described above. The result of theSP-HPLC analysis of the conversion of γ-linolenic acid with V531F is shown in FIG. 6. The following Table 2 shows a comparison of the specificity of the wild-type (cslbLOX) with the mutant (cslbLOXV$_{531}$F).

TABLE 2

Comparison of the product specificity of cslbLOX and cslbLOX$_{531}$F with γ-linolenic acid

| Enzyme | (13S, HE, 9Z, 6Z). 18:2 | (10S, 12Z, 8E, 6Z) –18:2 | (9S, 12Z, 10E, 6Z) –18:2 | (6S, 12Z, 9Z, 7E) 18:2 |
|---|---|---|---|---|
| cslbLOX | 80% | 17% | 2% | 0% |
| cslbLOXV$_{531}$mF | 26% | 14% | 9% | 51% |

3. Description of the Figures

FIG. 1 shows that the positional specificity of the LOX reaction depends on the site of the splitting off of the hydrogen and on the orientation of the radical. The [+2]-order of the radical shows that the oxygen is transferred to the second carbon atom in the direction of the methyl terminal of the substrate, counted from the site of the hydrogen removal. [−2] shows the inverse orientation of the ordering of the radical.

Figure 2:
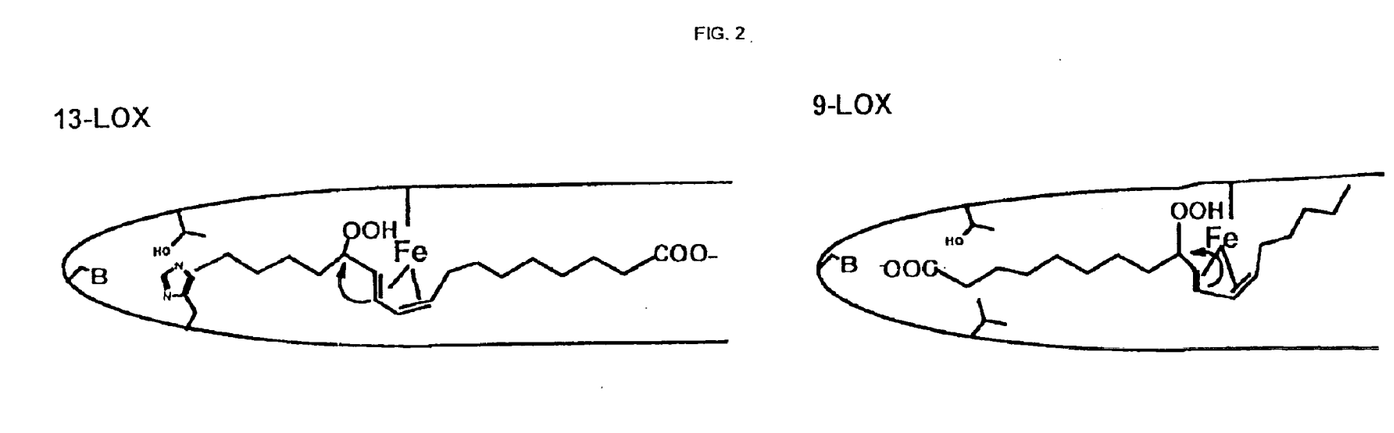
FIG. 2 shows the direct and inverse orientation of the substrate in the active centre of the LOX.

FIG. 2 shows the direct and inverse substrate orientation at the active site of the LOX (modified from Gardner, H. W. (1989) Biochem. Biophys. Acta 1001, 274–281).

Figure 3:
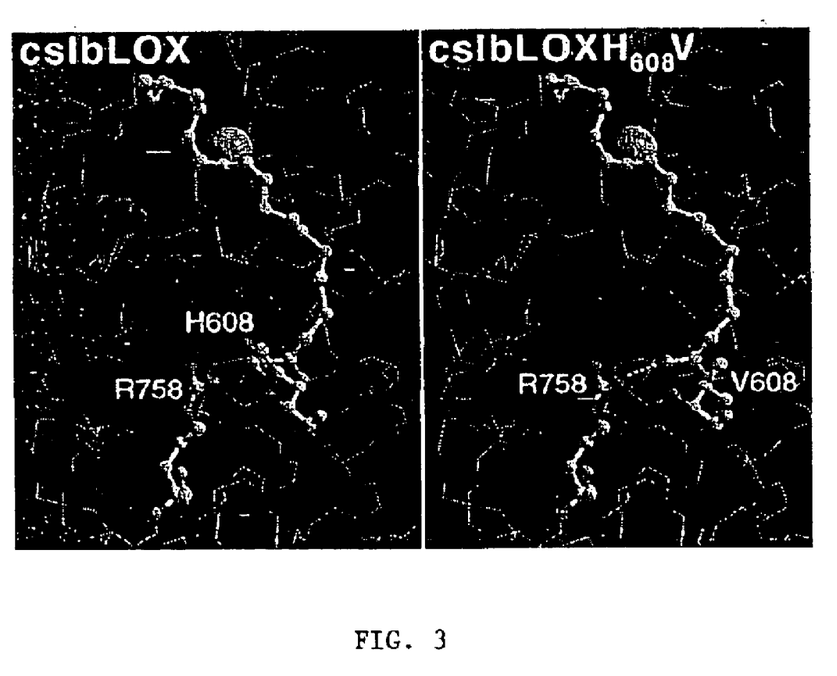
FIG. 3 shows a model of the enzyme substrate interaction of the wild-type LOX from cucumber and of the mutant H608V (corresponding to H597V, where in the latter nomenclature the numeration according to the sequence from FIG. 5 is used).

FIG. 3 shows a 3-dimensional model of the enzyme-substrate exchange operation. In the illustration on the left the wild-type enzyme is shown. Here the methyl terminal of the fatty acid substrate comes into contact with the sidechain H608. The charged residue R758 is screened by the residue H608. In the illustration on the right the mutant H608V (a H597V) is shown. In the inverse orientation the negatively charged carboxyl group of the substrate can form a salt bridge with the positively charged nitrogen of R758.

Figure 4:
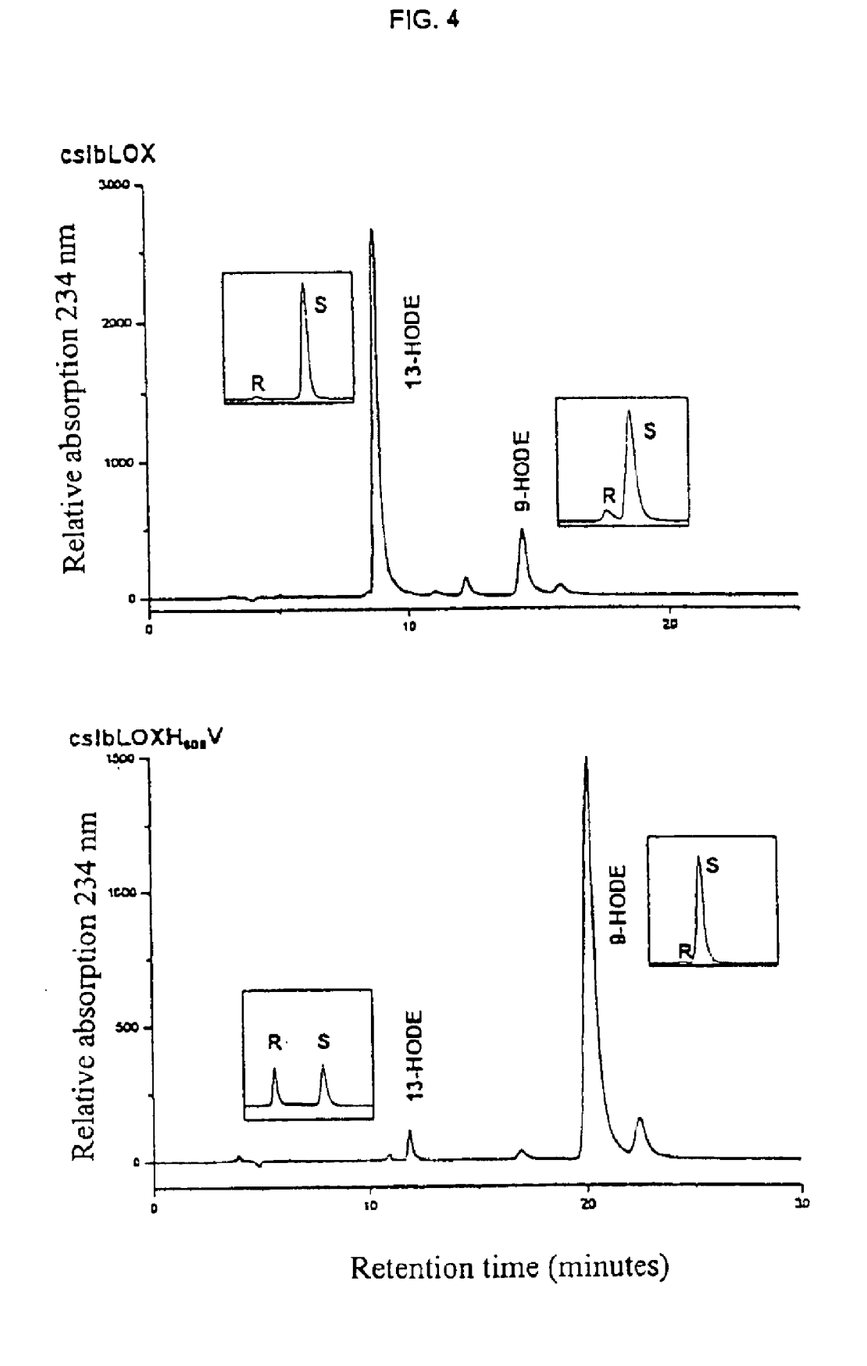
FIG. 4 shows the HPLC analysis of hydroxylated fatty acids procured with the aid of wild-type LOX from cucumber and of the H597V mutant from LA.

FIG. 4 shows the HPLC analysis of fatty acids with the mutant H597V. Equal quantities of LOX protein are incubated with 0.9 mM LA at room temperature for 30 minutes. Following reduction of the lipids with sodium borhydride the reaction mixture is acidified to pH 3 with acetic acid and the lipids extracted. The oxygenated fatty acid derivatives are isolated by means of RP-HPLC and the individual position isomers analysed with the aid of SP-HPLC. The proportions of S and R are analysed with the aid of CP-HPLC (inserted illustrations).

Figure 5:
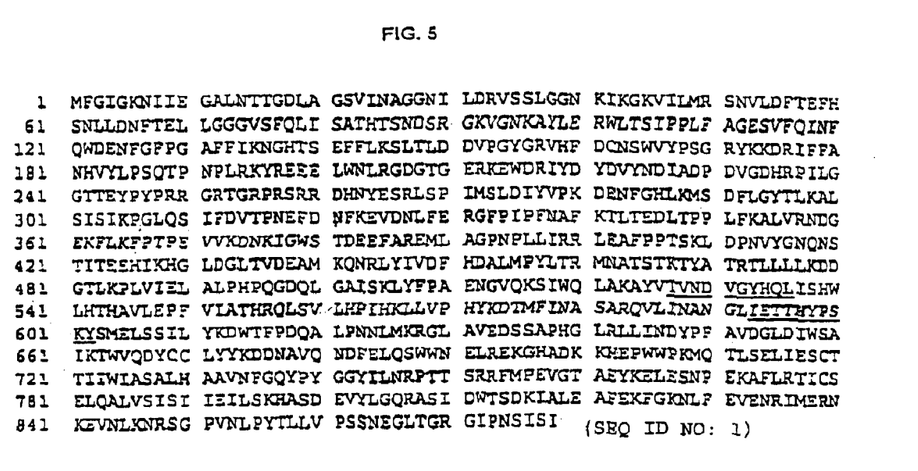
FIG. 5 shows the sequence of wild-type LOX from *Cucumis sativus*.

FIG. 5 shows the amino-acid sequence of wild-type lipoxygenase from *Cucumis sativus*.

FIG. 6 shows the HPLC analysis of the fatty acid pattern as obtained with the mutant V5321F and γ-linolenic acid.

Figure 7:
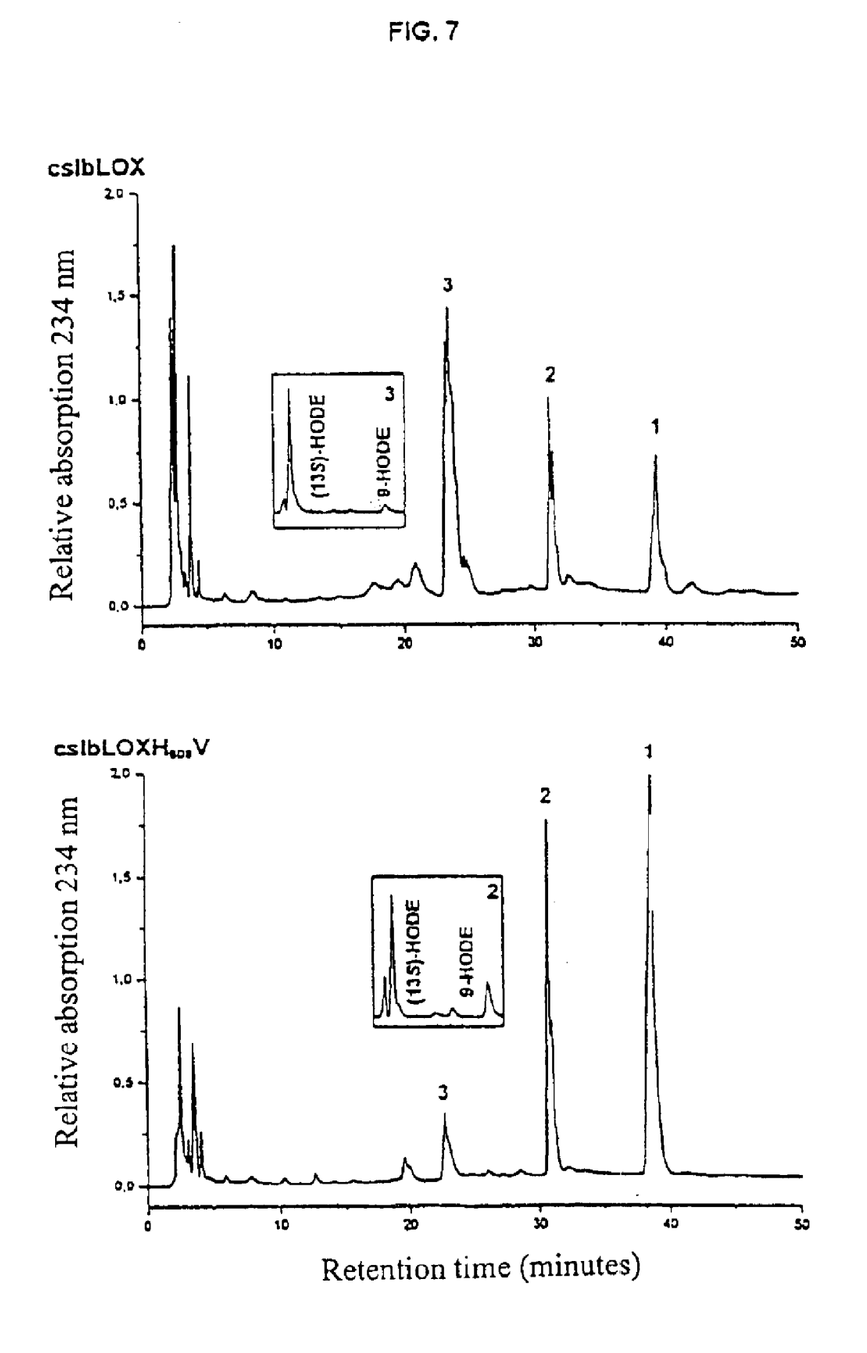
FIG. 7 shows the HPLC analysis of oxidated trilinolein, formed by wild-type enzyme and H597V mutants.

FIG. 7 shows the HPLC analysis of oxidized trilinolein as a result of conversion with the wild-type enzyme or the mutant H597V. Equal quantities of LOX protein were incubated with an emulsion from 1.2 mM TL for 30 minutes. The lipids were reduced with sodium borhydride and the reaction mixture acidified to pH 3 with glacial acetic acid. Following extraction of the lipids the analysis continued by means of RP-HPLC. A representative chromatogram of this analysis is shown. The numbers identify the LOX reaction products obtained: 1 means a TL derivative containing an oxygenated fatty acid; 2 means a doubly oxygenated TL isomer, and 3 means a TL oxygenated three times. For analysis of the positional isomers of LA residues the free fatty acid derivatives were obtained by means of alkaline hydrolysis and subsequent RP-HPLC. The positional isomers of hydroxylinoleic acid (HODE) were represented as molar ratios as determined by means of SP-HPLC, as shown in the accompanying illustrations. Optical isomers were ascertained by means of CP-HPLC The Abbreviations Used are:
  CP-HPLC for chiral phase HPLC;
  RP-HPLC for reverse phase HPLC;
  SP-HPLC for direct phase HPLC;
  HPETE for hydroperoxyarachidonic acid
  13-H(P)ODE for (13S, 9Z, 11E)-13-hydro(pero)xy-9,11-octadecylic acid;
  9(HP)ODE for (9S, 10E, 12Z)-9-hydro(pro)xy-10,12-octadecylic acid;
  LA for linoleic acid;
  LOX for lipoxygenase;
  L for trilinolein.

SUMMARY

The present invention concerns a procedure for the manufacture of plant lipoxygenases with altered positional specificity as well as the lipoxygenase obtained through the procedure and its use for the hydroperoxylation of substrates. In particular the LOXs according to the invention permit for the first time the manufacture of new γ-linolenic acid derivatives in large quantity. For this γ-linolenic acid as substrate is incubated under suitable conditions with the LOXs according to the invention. Depending on the mutant LOXs put into use a hydroperoxylation of the γ-linolenic acid the ensues, preferably at position 6 or position 9 or positions 6 and

What is claimed is:

1. A lipoxygenase from *Cucumis sativus* comprising the amino acid sequence of SEQ ID NO: 1 except that one or more amino acids in positions 527 to 536 and 593 to 602 of SEQ ID NO: 1 are substituted with a different amino acid.

2. The lipoxygenase of claim 1, comprising a substitution at amino acid position 531 and/or 597 of SEQ ID NO: 1.

3. The lipoxygenase of claim 2, wherein the amino acid at position 531 of SEQ ID NO: 1 is substituted with a Phe- or His-residue and/or the amino acid at position 597 of SEQ ID NO: 1 is substituted with a Val- or Phe-residue.

4. The lipoxygenase of claim 3, wherein the amino acid at position 531 of SEQ ID NO: 1 is substituted with a Phe-residue and/or the amino acid at position 597 of SEQ ID NO: 1 is substituted with a Val-residue.

* * * * *

SEQUENCE LISTING

<160> NUMBER OF SEQ ID NOS: 5

<210> SEQ ID NO 1
<211> LENGTH: 878
<212> TYPE: PRT
<213> ORGANISM: Cucumis sativus

<400> SEQUENCE: 1

```
Met Phe Gly Ile Gly Lys Asn Ile Ile Glu Gly Ala Leu Asn Thr Thr
 1               5                  10                  15

Gly Asp Leu Ala Gly Ser Val Ile Asn Ala Gly Gly Asn Ile Leu Asp
            20                  25                  30

Arg Val Ser Ser Leu Gly Gly Asn Lys Ile Lys Gly Lys Val Ile Leu
        35                  40                  45

Met Arg Ser Asn Val Leu Asp Phe Thr Glu Phe His Ser Asn Leu Leu
    50                  55                  60

Asp Asn Phe Thr Glu Leu Leu Gly Gly Gly Val Ser Phe Gln Leu Ile
65                  70                  75                  80

Ser Ala Thr His Thr Ser Asn Asp Ser Arg Gly Lys Val Gly Asn Lys
                85                  90                  95

Ala Tyr Leu Glu Arg Trp Leu Thr Ser Ile Pro Pro Leu Phe Ala Gly
            100                 105                 110

Glu Ser Val Phe Gln Ile Asn Phe Gln Trp Asp Glu Asn Phe Gly Phe
        115                 120                 125

Pro Gly Ala Phe Phe Ile Lys Asn Gly His Thr Ser Glu Phe Phe Leu
```

```
            130                 135                 140
Lys Ser Leu Thr Leu Asp Asp Val Pro Gly Tyr Gly Arg Val His Phe
145                 150                 155                 160

Asp Cys Asn Ser Trp Val Tyr Pro Ser Gly Arg Tyr Lys Lys Asp Arg
                165                 170                 175

Ile Phe Phe Ala Asn His Val Tyr Leu Pro Ser Gln Thr Pro Asn Pro
                180                 185                 190

Leu Arg Lys Tyr Arg Glu Glu Glu Leu Trp Asn Leu Arg Gly Asp Gly
                195                 200                 205

Thr Gly Glu Arg Lys Glu Trp Asp Arg Ile Tyr Asp Tyr Asp Val Tyr
                210                 215                 220

Asn Asp Ile Ala Asp Pro Asp Val Gly Asp His Arg Pro Ile Leu Gly
225                 230                 235                 240

Gly Thr Thr Glu Tyr Pro Tyr Pro Arg Arg Gly Arg Thr Gly Arg Pro
                245                 250                 255

Arg Ser Arg Arg Asp His Asn Tyr Glu Ser Arg Leu Ser Pro Ile Met
                260                 265                 270

Ser Leu Asp Ile Tyr Val Pro Lys Asp Glu Asn Phe Gly His Leu Lys
                275                 280                 285

Met Ser Asp Phe Leu Gly Tyr Thr Leu Lys Ala Leu Ser Ile Ser Ile
                290                 295                 300

Lys Pro Gly Leu Gln Ser Ile Phe Asp Val Thr Pro Asn Glu Phe Asp
305                 310                 315                 320

Asn Phe Lys Glu Val Asp Asn Leu Phe Glu Arg Gly Phe Pro Ile Pro
                325                 330                 335

Phe Asn Ala Phe Lys Thr Leu Thr Glu Asp Leu Thr Pro Pro Leu Phe
                340                 345                 350

Lys Ala Leu Val Arg Asn Asp Gly Glu Lys Phe Leu Lys Phe Pro Thr
                355                 360                 365

Pro Glu Val Val Lys Asp Asn Lys Ile Gly Trp Ser Thr Asp Glu Glu
                370                 375                 380

Phe Ala Arg Glu Met Leu Ala Gly Pro Asn Pro Leu Leu Ile Arg Arg
385                 390                 395                 400

Leu Glu Ala Phe Pro Pro Thr Ser Lys Leu Asp Pro Asn Val Tyr Gly
                405                 410                 415

Asn Gln Asn Ser Thr Ile Thr Glu Glu His Ile Lys His Gly Leu Asp
                420                 425                 430

Gly Leu Thr Val Asp Glu Ala Met Lys Gln Asn Arg Leu Tyr Ile Val
                435                 440                 445

Asp Phe His Asp Ala Leu Met Pro Tyr Leu Thr Arg Met Asn Ala Thr
                450                 455                 460

Ser Thr Lys Thr Tyr Ala Thr Arg Thr Leu Leu Leu Lys Asp Asp
465                 470                 475                 480

Gly Thr Leu Lys Pro Leu Val Ile Glu Leu Ala Leu Pro His Pro Gln
                485                 490                 495

Gly Asp Gln Leu Gly Ala Ile Ser Lys Leu Tyr Phe Pro Ala Glu Asn
                500                 505                 510

Gly Val Gln Lys Ser Ile Trp Gln Leu Ala Lys Ala Tyr Val Thr Val
                515                 520                 525

Asn Asp Val Gly Tyr His Gln Leu Ile Ser His Trp Leu His Thr His
                530                 535                 540

Ala Val Leu Glu Pro Phe Val Ile Ala Thr His Arg Gln Leu Ser Val
545                 550                 555                 560
```

-continued

```
Leu His Pro Ile His Lys Leu Leu Val Pro His Tyr Lys Asp Thr Met
                565                 570                 575
Phe Ile Asn Ala Ser Ala Arg Gln Val Leu Ile Asn Ala Asn Gly Leu
            580                 585                 590
Ile Glu Thr Thr His Tyr Pro Ser Lys Tyr Ser Met Glu Leu Ser Ser
        595                 600                 605
Ile Leu Tyr Lys Asp Trp Thr Phe Pro Asp Gln Ala Leu Pro Asn Asn
    610                 615                 620
Leu Met Lys Arg Gly Leu Ala Val Glu Asp Ser Ser Ala Pro His Gly
625                 630                 635                 640
Leu Arg Leu Leu Ile Asn Asp Tyr Pro Phe Ala Val Asp Gly Leu Asp
                645                 650                 655
Ile Trp Ser Ala Ile Lys Thr Trp Val Gln Asp Tyr Cys Cys Leu Tyr
            660                 665                 670
Tyr Lys Asp Asp Asn Ala Val Gln Asn Asp Phe Glu Leu Gln Ser Trp
        675                 680                 685
Trp Asn Glu Leu Arg Glu Lys Gly His Ala Asp Lys Lys His Glu Pro
    690                 695                 700
Trp Trp Pro Lys Met Gln Thr Leu Ser Glu Leu Ile Glu Ser Cys Thr
705                 710                 715                 720
Thr Ile Ile Trp Ile Ala Ser Ala Leu His Ala Ala Val Asn Phe Gly
                725                 730                 735
Gln Tyr Pro Tyr Gly Gly Tyr Ile Leu Asn Arg Pro Thr Thr Ser Arg
            740                 745                 750
Arg Phe Met Pro Glu Val Gly Thr Ala Glu Tyr Lys Glu Leu Glu Ser
        755                 760                 765
Asn Pro Glu Lys Ala Phe Leu Arg Thr Ile Cys Ser Glu Leu Gln Ala
    770                 775                 780
Leu Val Ser Ile Ser Ile Ile Glu Ile Leu Ser Lys His Ala Ser Asp
785                 790                 795                 800
Glu Val Tyr Leu Gly Gln Arg Ala Ser Ile Asp Trp Thr Ser Asp Lys
                805                 810                 815
Ile Ala Leu Glu Ala Phe Glu Lys Phe Gly Lys Asn Leu Phe Glu Val
            820                 825                 830
Glu Asn Arg Ile Met Glu Arg Asn Lys Glu Val Asn Leu Lys Asn Arg
        835                 840                 845
Ser Gly Pro Val Asn Leu Pro Tyr Thr Leu Leu Val Pro Ser Ser Asn
    850                 855                 860
Glu Gly Leu Thr Gly Arg Gly Ile Pro Asn Ser Ile Ser Ile
865                 870                 875

<210> SEQ ID NO 2
<211> LENGTH: 10
<212> TYPE: PRT
<213> ORGANISM: Artificial
<220> FEATURE:
<223> OTHER INFORMATION: Synthetic

<400> SEQUENCE: 2

Thr Val Asn Asp Val Gly Tyr His Gln Leu
1               5                   10

<210> SEQ ID NO 3
<211> LENGTH: 10
<212> TYPE: PRT
<213> ORGANISM: Artificial
```

```
<220> FEATURE:
<223> OTHER INFORMATION: Synthetic

<400> SEQUENCE: 3

Ile Glu Thr Thr His Tyr Pro Ser Lys Tyr
1               5                   10

<210> SEQ ID NO 4
<211> LENGTH: 59
<212> TYPE: DNA
<213> ORGANISM: Artificial
<220> FEATURE:
<223> OTHER INFORMATION: Oligonucleotide primer

<400> SEQUENCE: 4
gcttatgtaa ctgttaatga tttcggttac catcaactta ttagtcattg gttgcatac        59

<210> SEQ ID NO 5
<211> LENGTH: 57
<212> TYPE: DNA
<213> ORGANISM: Artificial
<220> FEATURE:
<223> OTHER INFORMATION: Oligonucleotide primer

<400> SEQUENCE: 5
gtatgcaacc aatgactaat aagttgatgg taaccgaaat cattaacagt tacataa          57
```